(12) United States Patent
Jacobson

(10) Patent No.: US 6,452,060 B2
(45) Date of Patent: Sep. 17, 2002

(54) METHOD TO PREPARE CYCLOPROPENES

(75) Inventor: Richard Martin Jacobson, Chalfont, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/826,058

(22) Filed: Apr. 4, 2001

Related U.S. Application Data

(60) Provisional application No. 60/196,536, filed on Apr. 11, 2000.

(51) Int. Cl.$^7$ .................................. C07C 1/00
(52) U.S. Cl. ................. 585/638; 585/638; 585/641; 585/642; 568/669; 568/670
(58) Field of Search ................. 585/641, 638, 585/642; 568/669, 670

(56) References Cited

U.S. PATENT DOCUMENTS 5,723,714 A   3/1998   Binger ................. 585/638

FOREIGN PATENT DOCUMENTS

DE   4333491 A1   4/1995

OTHER PUBLICATIONS

Koester et al, Liebigs Ann. Chem. (1973), (7), 1219–35; English translation provided by the applicant.*

Cyclopropene: A New Simple Synthesis and Diels–Alder Reactions with Cyclopentadiene and 1,3–Diphenylisobenzofuran J. Org. Chem 1996, 61, 6462–6464.

J. Org. Chem., vol. 36, No. 9, 1971 pp. 1320 and 1321 An Efficient and Convenient Synthesis of 1–Methylcyclopropene.

Jun. 1965 p. 2089 & 2090 vol. 30 Synthesis of 1–Methylcyclopropene.

Translation of the German reference, Methylenecyclopropane and 1– and 3–Methylcyclopropene from Methallyl Chlorides and Alkali Amides Liebigs Ann. Chem. 1973, 1219–1235.

* cited by examiner

Primary Examiner—Sreeni Padmanabhan
Assistant Examiner—Farhad Forohar
(74) Attorney, Agent, or Firm—Thomas D. Rogerson; Gregory M. Hill

(57) ABSTRACT

The present invention relates to a method to prepare cyclopropenes.

3 Claims, No Drawings

METHOD TO PREPARE CYCLOPROPENES

CROSS REFERENCE TO RELATED PATENT APPLICATIONS

This is a non-provisional application of prior pending U.S. provisional application No. 60/196,536 Titled "A METHOD TO PREPARE CYCLOPROPENES", filed Apr. 11, 2000.

The present invention relates to a method to prepare cyclopropenes.

Cyclopropenes have a variety of uses in the chemical industry. One recent discovery is the ability of 1-methylcyclopropene, and related analogs, to inhibit the action of ethylene on plants (see U.S. Pat. No. 5,518,988). Several syntheses for cyclopropene and its simple derivatives have been reported. The most widely practiced process is the sodium amide induced α-elimination of an allylic chloride (see F. Fisher and D. Applequist, *J. Org. Chem.*, 30, 2089 (1965)). Unfortunately, this method suffers from relatively low yields, difficulty in purifying the final product, and the use of excess sodium amide. An improved synthesis of 1-methylcyclopropene incorporates the use of freshly prepared halide free phenyllithium as the base replacing sodium amide. This method provides overall yields in the 60 to 80 percent range (see R. Magid, et. al., *J. Org. Chem.*, 36, 1320 (1971)). Similar synthesis methods are disclosed in U.S. Pat. No. 6,017,849.

Although the reported reactions work reasonably well, a major problem often encountered is the presence of unwanted isomers such as methylenecyclopropane in the final product mixture. Methods which improve the isomer ratio (that is, increased 1-methylcyclopropene compared to the methylenecyclopropane often do so at the expense of overall yield of product (see Koster, et. al., *Liebigs Ann. Chem.*, 1219 (1973)). Because of these problems, there is still a need for a method to prepare 1-methylcyclopropene in high yield and in high isomer purity. I have discovered that when a catalytic amount of certain weaker bases is added to the reaction mixture of a substituted or unsubstituted allyl halide and a strong base in an inert solvent, cyclopropenes, with greatly reduced unwanted isomer content, are produced in high yield.

The present invention, therefore, is a method to prepare cyclopropenes, comprising combining an allyl compound of formula I:

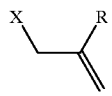

I wherein:
  X is a leaving group; and
  R is hydrogen or a substituted or unsubstituted alkyl, alkenyl, alkynyl, cycloalkyl, cycloalkylalkyl, phenyl, or naphthyl group; wherein the substituents are independently halogen, alkoxy, or substituted or unsubstituted phenoxy;
with a non-nucleophilic strong base in an inert solvent in the presence of a catalytic amount of a weaker, non-nucleophilic base.

As used herein, the term "alkyl" means both straight and branched chain ($C_1$–$C_{20}$) radicals which include, for example, methyl, ethyl, n-propyl, isopropyl, 1-ethylpropyl, n-butyl, tert-butyl, isobutyl, 2,2-dimethylpropyl, pentyl, octyl, and decyl. The terms "alkenyl" and "alkynyl" mean ($C_3$–$C_{20}$) alkenyl and alkynyl groups such as, for example, 2-propenyl, 2-butenyl, 3-butenyl, 2-methyl-2-propenyl, and 2-propynyl. The term "cycloalkylalkyl" means a ($C_1$–$C_{15}$) alkyl group substituted with a ($C_3$–$C_6$) cycloalkyl group such as, for example cyclopropylmethyl, cyclopropylethyl, cyclobutylmethyl, and cyclopentylethyl. The term "haloalkyl" means an alkyl radical wherein one or more of the hydrogen atoms have been replaced by a halogen atom. The term "halogen" means fluorine, chlorine, bromine, and iodine. The term "strong base" means a non-nucleophilic base with a $pK_a$ greater than 35. The term "weaker base" means a non-nucleophilic base with a $pK_a$ of from 26 to 35, or the conjugate acid thereof. The term "inert solvent" means a solvent which does not react with the strong base, the weaker base, the allyl halide, or the resulting cyclopropene.

As used herein, all percentages are percent by weight, unless otherwise specified and are inclusive and combinable. All ratios are by weight and all ratio ranges are inclusive and combinable. All molar ranges are inclusive and combinable.

Preferably, X is a leaving group selected from halogen, alkyl or aryl sulfonyloxy, alkyl or aryl sulfate, and alkoxy. More preferably, X is chloro, bromo, iodo, benzenesulfonyloxy, p-toluenesulfonyloxy, methanesulfonyloxy, or t-butoxy. Even more preferably, X is chloro, bromo, or benzenesulfonyloxy. Most preferably, X is chloro or bromo.

Preferably, R is ($C_1$–$C_{10}$) alkyl. More preferably, R is ($C_1$–$C_8$) alkyl. Most preferably, R is methyl.

Preferably, the inert solvent is an aliphatic or aromatic hydrocarbon such as, for example, mineral oil, benzene, toluene, or xylene; an ether such as, for example, diethyl ether, tetrahydrofuran, or dioxane, a halogenated hydrocarbon such as, for example perhaloalkanes or methylene chloride, liquid ammonia, or lower alkyl amine or lower dialkyl amine such as, for example, methylamine or dimethylamine. More preferably, the solvent is an aliphatic or aromatic hydrocarbon. Most preferably, the solvent is mineral oil. The solvent may be a mixture of more than one inert solvent.

Preferably, the strong base is an alkali metal salt of an amine or an organometallic base. More preferably, the strong base is sodium, potassium, or lithium amide or phenyllithium. Most preferably, the strong base is sodium amide. The strong base may be a mixture of more than one strong base. The amount of strong base used in the method will vary depending upon the weaker base used, the inert solvent, and the temperature at which the reaction is conducted. Preferably, the amount of strong base used is from 0.1 to 20 moles per mole of allyl compound of formula I. More preferably the amount of strong base used is from 0.5 to 2 moles per mole of allyl compound of formula I. Most preferably, the amount of strong base used is from 0.7 to 1.4 moles per mole of allyl compound of formula I.

Preferably, the weaker base is soluble in the inert solvent. More preferably, the weaker base is a silyl amine, a disilazane, their cyclic analogs, mixed cyclic silazane/ether analogs, or metal salts thereof. Even more preferably, the weaker base is a silyl amine or a disilazane. Still more preferably, the weaker base is a dialkyl- or trialkyl, diaryl- or triaryl, or mixed alkyl/aryl silyl amine; a tetraalkyl-, pentaalkyl- or hexaalkyl, tetraaryl-, pentaaryl-, or hexaaryl, or mixed alkyl/aryl disilazane; or their cyclic analogs. Still more preferably, the weaker base is 1,1,1-triphenylsilylamine, tri-n-hexylsilylamine, 1,1,1,3,3,3-hexamethyldisilazane, 1,1,3,3-tetramethyldisilazane, 2,2,4, 4,6,6-hexamethylcyclotrisilazane, octamethylcyclotetrasilazane, hexaethyldisilazane, 1,3-di-n-octyltetramethyldisilazane, or 2,2,5,5-tetramethyl-2,5-disila-1-azacyclopentane. Most preferably, the weaker base is hexamethyldisilazane. The weaker base can be a mixture of more than one weaker base. The amount of weaker based used in the method of this invention will vary depending upon the strong based used, the inert solvent used, and the temperature at which the reaction is conducted. Preferably, the amount of weaker base used is from 0.001 to 0.95 moles per mole of strong base used. More preferably, the amount of weaker base used is from 0.02 to 0.4 moles per mole of strong base. Most preferably, the amount of weaker base used is from 0.02 to 0.2 moles per mole of strong base.

The order of addition of the reactants to the solvent is not critical. However, it is preferred that the allyl compound of formula I is added last to a mixture of the other components. Most preferably, the allyl compound is added slowly to a mixture of the other components.

The temperature at which the method of this invention is carried out is not critical. However, because cyclopropenes are reactive compounds, care must be taken to ensure either a) that the temperature is kept below that at which decomposition or side reactions occur, or b) the cyclopropene produced must be removed from the reaction mixture as it is being produced, or a combination of a) and b). Preferably, the cyclopropene produced will be distilled from the reaction mixture and collected in a cooled receiver as it is produced. For lower boiling cyclopropenes, the temperature is preferably greater than or equal to the boiling point of the cyclopropene and the cyclopropene is distilled from the reaction mixture as it is being produced. For higher boiling cyclopropenes, the temperature is preferably less than the decomposition temperature of the cyclopropene.

Preferably, the reaction mixture is stirred or otherwise agitated and/or sparged or purged with an inert gas during the reaction. Preferably the inert gas is nitrogen. More preferably, and particularly in the case of lower boiling cyclopropenes, the agitation rate is sufficiently high to ensure that the cyclopropene distills from the reaction mixture as soon as possible after being formed. Fast removal of the cyclopropene from the reaction mixture reduces production of side products such as alkylidenecyclopropanes and teleomers.

The pressure at which the reaction is conducted is also not critical. Ambient pressure is preferred. However, pressure or vacuum may be utilized to affect the relative boiling points of the cyclopropene produced and the inert solvent to aid in separation of the cyclopropene from the reaction mixture.

The method of this invention is illustrated by the following examples and comparative examples. In the following examples, all percentages and parts are by weight.

Preparation of 1-methylcyclopropene with catalysis:

Into a 1000 ml 4 necked round bottomed flask equipped with an internal thermometer, overhead stirring, a pressure equalizing addition funnel and a condenser was added 109 g (2.79 moles) of commercial sodium amide and 110 ml of light mineral oil. The flask was heated, via an external bath, to 45° C. internal temperature whereupon 4.2 g (0.03 moles) of hexamethyldisilazane was added. Over the course of 50 minutes, 202 g (2.23 moles) of 3-chloro-2-methylpropene was slowly added. The gas that was evolved was ducted through the condenser and then scrubbed with water and finally condensed in a dry ice cooled trap. Yield was 39.3 g of 1-methylcyclopropene contaminated with 1.5 percent of methylenecyclopropane and 8 percent of 3-chloro-2-methylpropene starting material. A simple distillation of the product gave a final product containing less than 0.1 percent 3-chloro-2-methylpropene.

Preparation of 1-methylcyclopropene in the absence of catalyst:

Into a 1000 ml 4 necked round bottomed flask equipped with an internal thermometer, overhead stirring, a pressure equalizing addition funnel and a condenser was added 33.4 g (0.856 moles) of commercial sodium amide and 100 ml of light mineral oil. The flask was heated, via an external bath, to 45° C. internal temperature. Over the course of 90 minutes, 36.7 g (0.405 moles) of 3-chloro-2-methylpropene was slowly added. No gas was evolved indicating either a) no 1-methylcyclopropene was produced or b) any 1-methylcyclopropene which was produced decomposed or engaged in further reaction(s).

I claim:

1. A method to prepare a cyclopropene, comprising combining an allyl compound of the formula:

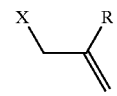

wherein:

X is a leaving group; and

R is hydrogen or a substituted or unsubstituted alkyl, alkenyl, alkynyl, cycloalkyl, cycloalkylalkyl, phenyl or naphthyl group wherein the substituents are independently halogen alkoxy, or substituted or unsubstituted phenoxy;

with a sodium amide in mineral oil in the presence of a catalytic amount of a non-nucleophilic, weaker base, selected from the group consisting of silyl amine and hexamethyldisilizane.

2. The method of claim 1, wherein the method further comprises removing the cyclopropene from the reaction mixture by distillation.

3. The method of claim 1, wherein R is methyl.

* * * * *